United States Patent [19]

Konobevtsev, deceased et al.

[11] Patent Number: 5,018,525

[45] Date of Patent: May 28, 1991

[54] DEVICE FOR DENTAL ELECTROANALGESIA

[75] Inventors: Oleg F. Konobevtsev, deceased, late of Moscow, by Irina V. Kazanskaya, administrator; Mikhail A. Napadov; Gennady G. Grishanin, both of Kharkov; Georgy S. Kuklin, Moscow; Gennady F. Krivulya; Sergei V. Guschin, both of Kharkov; Vladimir N. Kondaurov, Moskovskaya; Oleg A. Chelyapin; Ljudmila S. Slobodyanik, both of Kharkov; Jury P. Gusev, Moscow; Oleg J. Kondratenko, Kharkov; Vladimir I. Salo, Kharkov; Anatoly G. Shepenko, Kharkov, all of U.S.S.R.

[73] Assignees: Kharkovski Medicinsky Institute; Kharkovski Institut Radioelectroniki, both of Kharkov, U.S.S.R.

[21] Appl. No.: 430,613

[22] Filed: Nov. 1, 1989

[51] Int. Cl.$^5$ .......................... A61N 1/34; A61N 1/00
[52] U.S. Cl. .................................... 128/421
[58] Field of Search .................. 128/905, 421, 422; 600/26

[56] References Cited

U.S. PATENT DOCUMENTS

| | | | |
|---|---|---|---|
| 4,445,910 | 8/1990 | Budyho et al. | 128/421 |
| 4,782,837 | 11/1988 | Hogan | 128/421 |
| 4,784,142 | 11/1988 | Liss et al. | 128/421 |

Primary Examiner—William E. Kamm
Assistant Examiner—Scott R. Akess
Attorney, Agent, or Firm—Burgess, Ryan & Wayne

[57] ABSTRACT

A device for dental electroanalgesia includes a low-frequency electric pulse generator with an electric pulse repetition frequency setter, an electric pulse front discriminator, an electric pulse shaper, a current amplifier, a transformer, and an electric pulse amplitude regulator electrically connected to electrodes. The electrodes are placed on a corresponding reflexogenic zone of the auricular concha and on the mucosa of the alveolar process of one of the jaws within the area of the projection of the root apices of the patient's teeth. A temperature snesor is placed on the patient's face skin in the area of segmental innervation of the patient's dental tissues and is connected to an electric pulse duration regulator whose output is connected to the input of the electric pulse shaper.

2 Claims, 4 Drawing Sheets

DEVICE FOR DENTAL ELECTROANALGESIA

TECHNICAL FIELD

The present invention relates generally to electrotherapy and more specifically to devices for dental electroanalgesia.

BACKGROUND OF THE INVENTION

The present invention will find application for anesthesiological support of an operative interference involved in a stomatological manipulation, i.e., preparation of hard dental tissues for a fixed partial denture, as well as in tooth filling and in operative treatment of caries.

An analgesic effect of a pulsed electric current is based on activation of the antinociceptive organism's system, which causes a complete or partial blocking of nociceptive impulses' conduction. A distinguishing feature of such an analgesic technique resides not only in a reduced patient's appreciation of pain but also amelioration of his/her psychoemotional state and normalization of the patient's physical reactions.

One state-of-the-art device for electrostimulation of a patient's tissues is known to be extensively used currently. (SU, A, 1,034,650), said device comprising a low-frequency current pulse generator, a high-frequency current pulse generator, the outputs of both being connected to the inputs of an electric pulse front discriminator, which is a shift register. The device comprises also a pulse shaper based on series-connected a first flip-flop and an AND gate.

The output of the low-frequency generator is also connected to the input of the first flip-flop.

The output of the AND gate is connected to the input of a current amplifier, while the output of the current amplifier is connected to the primary winding of a transformer, and the secondary winding of the transformer is connected, via the shift register, to electrodes. The input of a second pulse shaper is connected to a resistor, while the output of the pulse shaper is connected to a first input of a second flip-flop. The other input of the second flip-flop is connected to the output of the high-frequency current pulse generator, while the output of the second flip-flop is connected to the other input of the AND gate. The high-frequency pulse generator produces a train of electric stimuli (pulses) of a predetermined adjustable duration and repetition frequency. The output voltage of the second flip-flop gates the pulses at the input of the AND gate so that those pulses are passed at the output of the AND gate whose duration is not in excess of a value preset by the low-frequency generator. The electric stimuli arrived from the output of the AND gate, are applied to the current amplifier, which is loaded with the transformer. The amplitude of electric pulses delivered by the transformer secondary is increased with an increase in the duration of the voltage pulses applied to the transformer primary, whereas the electric pulses from the transformer secondary are delivered to the electrodes.

To provide an analgesic effect in preparation of hard dental tissues the active electrodes of the device are applied to the skin of reflexogenic zones, such as, e.g., the auricular concha, while the passive electrodes of the device are applied to the patient's facial skin close to the area of an intended stomatological interference.

In a given device a definite pulse repetition frequency and duration are set by manual adjustment of a variable resistor, while the intensity of tissue electrostimulation at the place of application of the active electrodes is preset according to patient's subjective sense of intense vibration under the electrodes due to electric current flowing therealong. As a result of the electrostimulation process the patient's pain sensitivity threshold is increased and the intensity of vibration sense is reduced or disappears altogether. To provide an analgesic effect adequate to the patient's painful sensations during an operative interference the dentist increases the amplitude of the current pulses by manual adjustment of the variable resistor in order to increase the intensity of electrostimulation and to attain the original sensory acuity of electrostimulation. To provide an analgesic effect adequate to the intensity of the patient's painful sensations, it is necessary to correct the intensity of electrostimulation five or six times for 25 to 30 minutes by manual adjustment of the variable resistor.

Thus, the intensity of anesthesiologic electrostimulation depends on patient's subjective sensation, which is influenced by his/her psychoemotional state, and on the practical skill and experience of the dentist involved.

Manual adjustment in the course of electrostimulation results, in a prolonged period of time required for attaining an analgesic effect, affects adversely the adequacy of electroanalgesic effect to patient's painful sensations during surgery. The parameters of effective electric pulses, i.e., amplitude, repetition frequency and duration are not concerned with an individual dynamics of increasing the patient's pain sensitivity threshold. The device fails to provide prognostication of an analgesic effect of electrostimulation. Inadequacy of the analgesic effect to patient's painful sensations during surgery can be determined only in the course of a stomatologic interference according to patient's painful sensation.

SUMMARY OF THE INVENTION

It is an object of the invention to provide an analgesic effect produced by electric pulses adequate to affect a patient's painful sensations during an operative interference.

Said object is accomplished by that a device for dental electroanalgesia, comprising series-connected a low-frequency electric pulse generator with an electric pulse repetition frequency setter, an electric pulse front discriminator, an electric pulse shaper, a current amplifier, a transformer, and an electric pulse amplitude regulator electrically connected to at least two electrodes. According to the invention, the output of the electric pulse repetition frequency setter is connected to a first adjustment input of the low-frequency electric pulse generator and there are additionally incorporated a temperature sensor adapted to be placed on the patient's facial skin in the area of segmental innervation of the patient's dental tissues being prepared, and an electric pulse duration regulator whose input is connected to the output of the temperature sensor and its output is connected to the input of the electric pulse shaper, while the electrodes are placed on a corresponding reflexogenic zone of the auricular concha and on the mucosa of the alveolar process of one of the jaws within the area of the projection of the root apices of the patient's teeth being prepared.

It is expedient that, with a view to increasing the efficiency of dental electroanalgesia in response to a change in a patient's pain sensitivity threshold, the device should comprise additionally an electric pulse repetition frequency regulator whose input is connected to the output of the temperature sensor, while its output is connected to a second adjustment input of the low-frequency electric pulse generator.

Practical application of the present invention makes it possible to automatically adjust the parameters of the pulses generated, that is, repetition frequency and duration depending on patient's skin temperature as measured by the temperature sensor and is in effect an objective evidence of a patient's reduced painful sensation and a measure of a prolonged clinical effect of electroanalgesia applied to patient's tissues being operated upon. In the process of analgesia application the pulse duration is increased, while the pulse repetition frequency is reduced, thus retaining the patient's original sensation of tissue vibration under the electrodes when electric current flows therealong. This enables one to carry out dental electroanalgesia adequate to the intensity of patient's painful sensations during an operative interference.

BRIEF DESCRIPTION OF THE DRAWINGS

The present invention is illustrated by a detailed description of a device for dental electroanalgesia and some specific exemplary embodiments thereof with reference to the accompanying drawings, wherein.

DETAILED DESCRIPTION OF THE INVENTION

Figure 1:
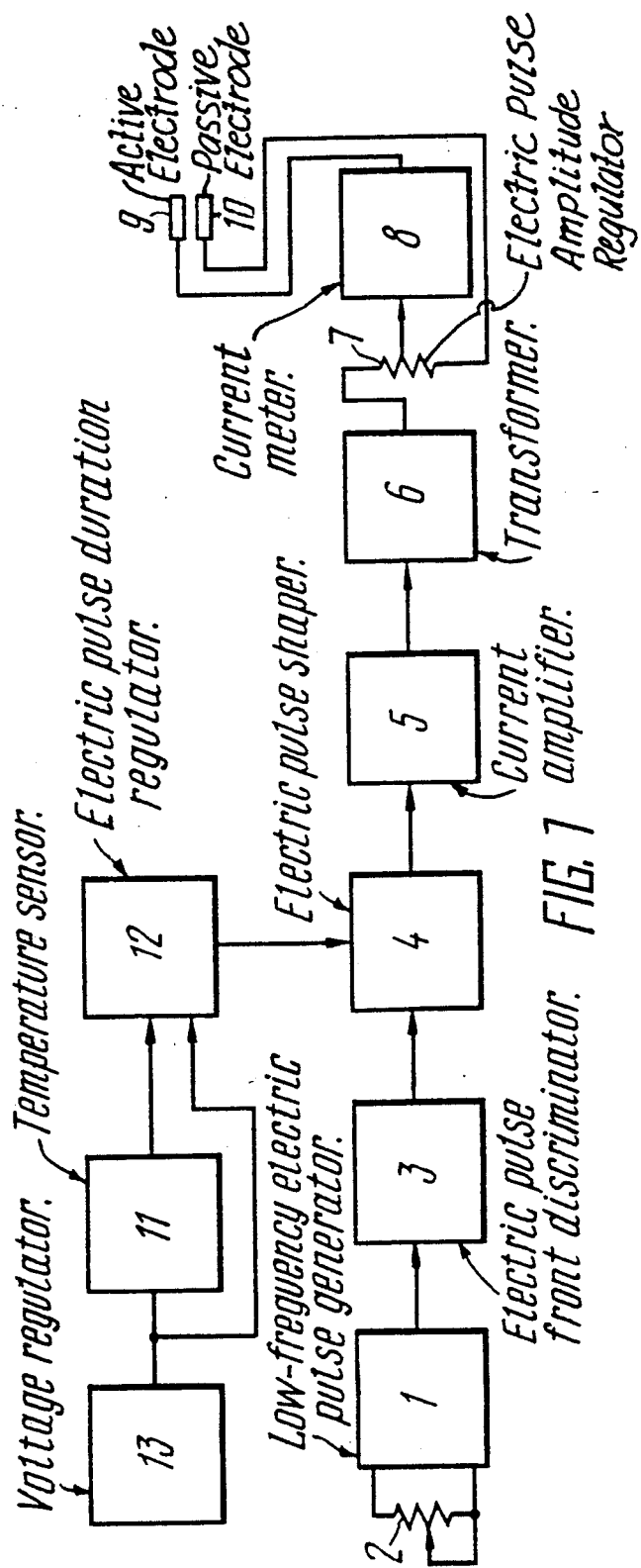
FIG. 1 presents a functional electric block diagram of a first embodiment of the device, according to the invention.

The device for dental electroanalgesia comprises series-connected a low-frequency electric pulse generator 1 (FIG. 1) with an electric pulse repetition frequency setter 2, an electric pulse front discriminator 3 made as a differentiating circuit, an electric pulse shaper 4, a current amplifier 5 and a stepup transformer 6, an electric pulse amplitude regulator 7, a current meter 8 connected to an active electrode 9 and a passive electrode 10. The active electrode 9 is placed on a reflexogenic zone of the patient's auricular concha innervated with a respective branch of the prigeminal nerve. The passive electrode 10 is placed on the mucosa of the vestibular surface of the alveolar process of one of the jaws within the area of the projection of the root apices of the patient's teeth being prepared. The device comprises also a temperature sensor 11 made as a thermoresistor placed on the skin of a patient's face in the area of segmental innervation of patient's dental tissues being prepared. The output of the temperature sensor 11 is connected to the input of an electric pulse duration regulator 12 made as a transistor-based amplifier. An alternative embodiment is possible, wherein the electric pulse duration regulator 12 is made as an electric element with variable parameters, e.g., a variable capacitor.

The output of the electric pulse duration regulator 12 is connected to the input of the electric pulse shaper 4. The input of the temperature sensor 11 and the input of the electric pulse duration regulator 12 are connected to the output of a voltage regulator 13.

Figure 2:
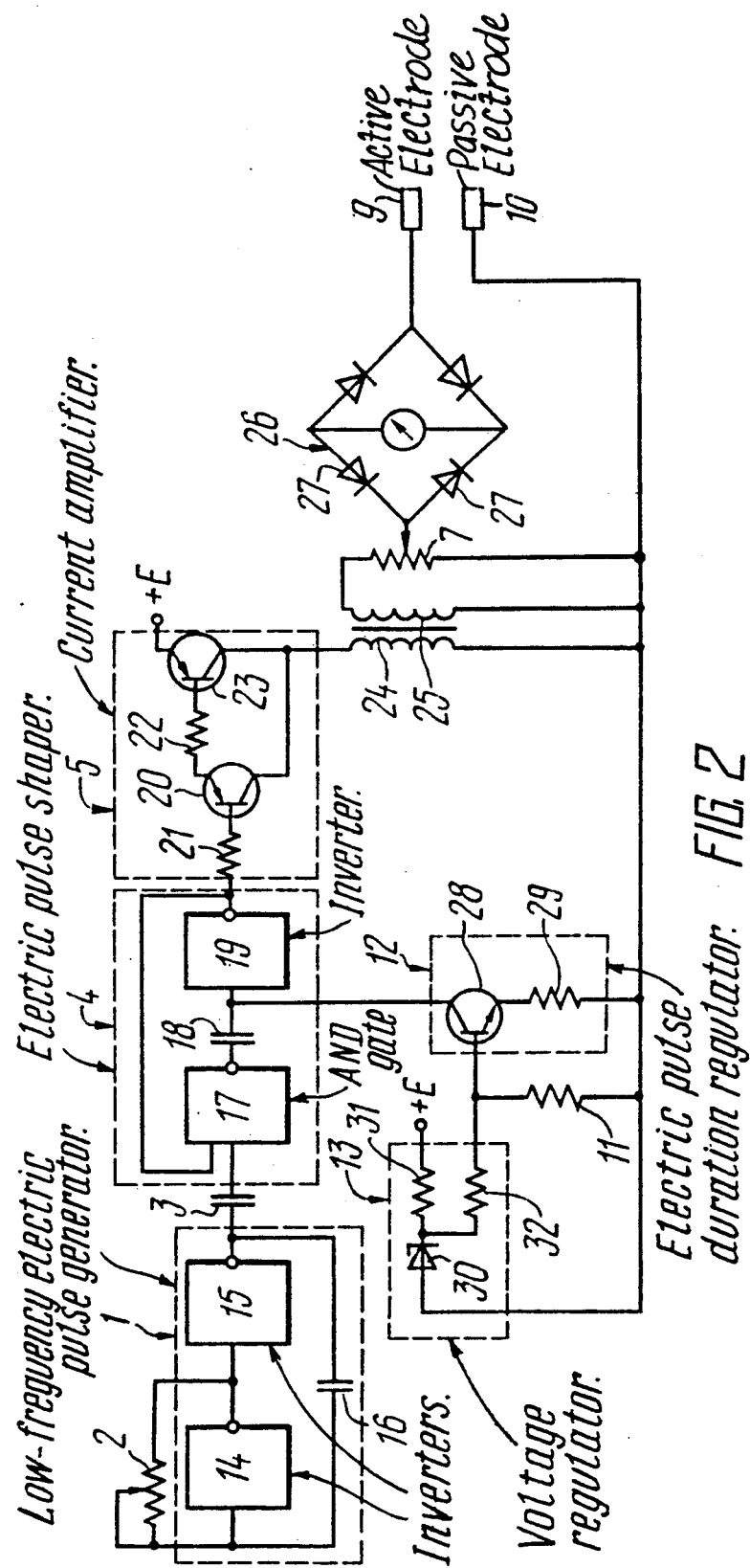
FIG. 2 is an elementary electric diagram of a first embodiment of the device, according to the invention.

In a specific embodiment of the device the lowfrequency electric pulse generator 1 (FIG. 2) is made as a first inverter 14 connected in parallel to the electric pulse repetition frequency setter 2 made as a variable resistor. The output of the inverter 14 is connected to the input of a second inverter 15. A capacitor 16 is connected to the output of the inverter 15 and to the input of the inverter 14. The electric pulse front discriminator 3 is made as a differentiating circuit, i.e., a capacitor in this particular case. The electric pulse shaper 4 is made as a one-shot multivibrator incorporating and AND gate 17, whose first input is connected to the output of the electric pulse front discriminator 3, while its output is connected, via a capacitor 18, to the input of an inverter 19. The output of the inverter 19 is connected to a second input of the AND gate 17. The current amplifier 5 is built around a composite transistor and comprises a first transistor 20 whose base is connected, via a resistor 21, to the output of the inverter 19 and its emitter is connected, via a resistor 22, to the base of a second transistor 23. The collector of the first transistor 20 is connected to the collector of the second transistor 23. The emitter of the second transistor 23 is connected to a voltage source (omitted in the Drawing). A primary winding 24 of the step-up transformer is connected to the collector of the second transistor 23. A secondary winding 25 of the step-up transformer 6 is connected to the terminals of the electric pulse amplitude regulator 7 made as a potentiometer. The current meter 8 is connected across a diagonally opposite pair of terminals of a bridge circuit 26 built around semiconductor diodes 27. The bridge circuit 26 is connected with one of its outputs to the control input of the electric pulse amplitude regulator 7 and with the other output, to the electrodes 9, 10.

The electric pulse duration regulator 12 is made as a transistor 28 whose collector is connected to the input of the inverter 19 of the electric pulse shaper 4, while the emitter is connected to a resistor 29, and the base is connected to the temperature sensor 11. The voltage stabilizer 13 comprises a Zener diode 30 connected, via a resistor 31, to a voltage source (omitted in the Drawing), and via a resistor 32, to the temperature sensor 11.

The device comprises also a common bus 33, which is connected to the negative pole of an electric power source (omitted in the Drawing). Connected to the common bus 33 are the passive electrode 10, the anode of the Zener diode 30, one of the outputs of the temperature sensor 11, the lead of the resistor 29, the leads of the primary winding 24 and the secondary winding 25 of the transformer 6, and one of the outputs of the electric pulse amplitude regulator 7.

With a view to adjusting the pulse repetition frequency the device comprises additionally an electric pulse repetition frequency regulator 34 (FIG. 3), which consists of a transistor 35 (FIG. 4) whose collector is connected to the input of the inverter 14 of the low-frequency electric pulse generator 1, while the emitter is connected to a resistor 36. The base of the transistor 35 is connected, via a resistor 37, to the resistor 32 of the electric pulse duration regulator 12, as well as to the cathode of a diode 38 whose anode is connected to the temperature sensor 11.

In addition, the electric pulse duration regulator 12 comprises also a diode 39 whose cathode is connected to the base of the transistor 28 and its anode is connected to the temperature sensor 11.

The device for dental electroanalgesia, according to the invention, operates as follows.

The active electrode 9 (FIG. 1) is applied to a corresponding reflexogenic zone of the auricular concha, while the passive electrode 10 is placed on the mucosa of the vestibular surface of the alveolar process of the upper or lower jaw in the area of the projection of the root apices of the patient's teeth being prepared. The temperature sensor 11 is placed on the skin of the patient's face in the area of segmental innervation of the patient's tissues being prepared, for instance, at the place of the projection of the infraorbital or mental foramen. Then the repetition frequency of the pulses produced by the lowfrequency generator is adjusted within 14 and 16 Hz with the aid of the electric pulse repetition frequency setter 2, whereupon the pulse amplitude is set against the patient's subjective sensation of a moderately intense vibration under the electrodes 9, 10, using the electric pulse amplitude regulator 7.

A change in the resistance value of the resistor of the electric pulse repetition frequency setter 2 results in a change of the discharge time constant of the capacitor 16 (FIG. 2) of the low-frequency electric pulse generator 1, whereby the repetition frequency of the pulses produced by the generator 1 is altered. Next the one-shot multivibrator of the pulse shaper 4 is triggered against the leading edge of an output electric pulse delivered from the output of the generator 1 through the electric pulse front discriminator 3 to the input of the electric pulse shaper 4. As a result, electric pulses are delivered from the output of the pulse shaper 4, the duration of which pulses depends on the resistance value of the electric pulse duration regulator 12. The resistance value of the regulator 12 depends in turn on the temperature of the patient's face skin as measured by the temperature sensor 11. With a certain approximation the resistance value of the temperature sensor 11 is in linear relationship with the temperature of the patient's face skin, therefore the duration of electric pulses passing through the patient's face skin located between the active electrode 9 and the passive electrode 10 is also in linear relationship with the skin temperature.

The voltage regulator 13 provides for stable regulation of electric pulses for duration and repetition frequency in response to a change in the voltage of a power source (omitted in the Drawing).

The one-shot multivibrator of the pulse shaper 4 is triggered by the positive electric pulses delivered from the output of the electric pulse front discriminator 3. As a result, the AND gate 17 is enabled, and the capacitor 18 of the pulse shaper 4 discharges. The inverter 19 of the pulse shaper 4 is disabled during discharge of the capacitor 18. The resistance value of the temperature sensor 11 decreases depending on an increase in the temperature of the patient's face skin, whereby the transistor 28 of the regulator 12 is disabled, its internal resistance increases and duration of the output electric pulses of the shaper 4 is increased, too. All the time while the one-shot multivibrator of the pulse shaper 4 is enabled the inverter 19 is disabled, which enables the composite transistor of the current amplifier 5 based on the transistors 20 and 23. With the transistor 23 enabled electric current is free to flow through the primary winding 24 of the transformer 6 and the common bus 33 of the device.

Voltage pulses are induced in the secondary winding 25 of the transformer 6, the value of said pulses being adjusted with the aid of the electric pulse amplitude regulator 7.

The mean value of the output electric pulses is measured by means of the current meter 8 connected between diagonally opposite pairs of terminals of the bridge circuit 26. Electric pulses are applied to the active electrode 9 through the bridge circuit 26 and the current meter 8. Thus, electric current flows along a circuit incorporating the active electrode 9, the patient's tissues, the passive electrode 10, the common bus 33 of the device.

Figure 3:
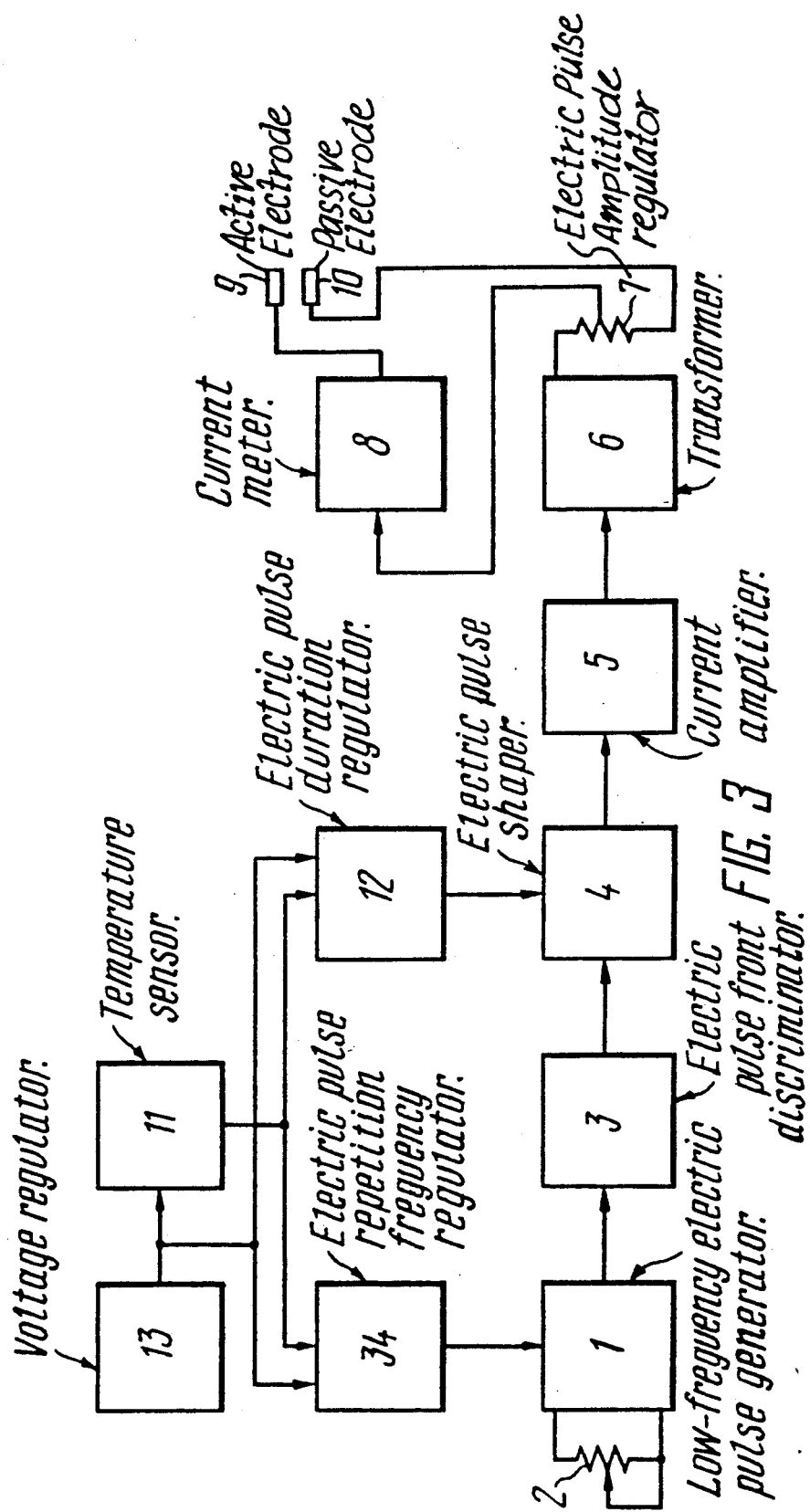
FIG. 3 shows a functional electric block diagram of a second embodiment of the device, according to the invention.
Figure 4:
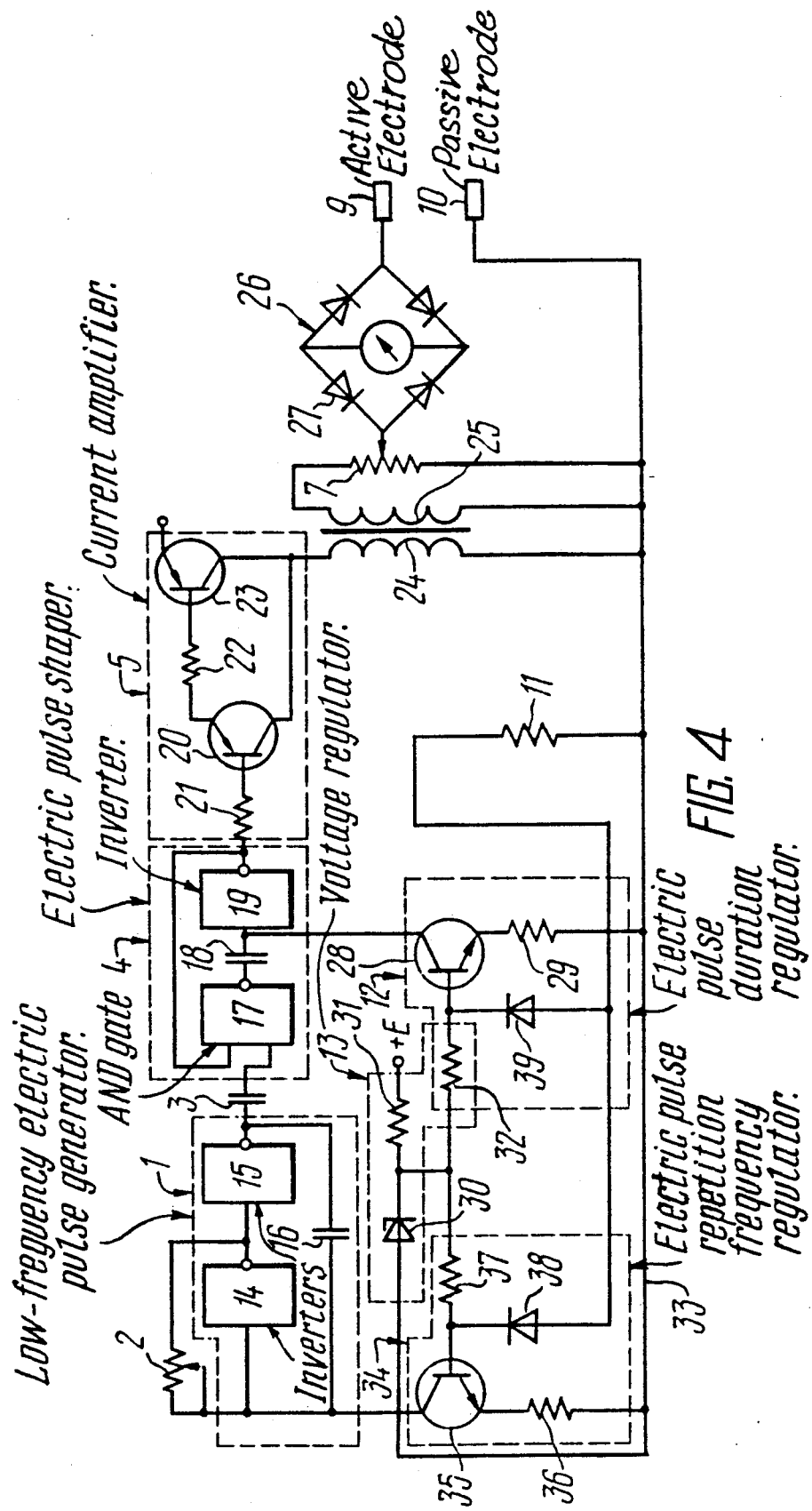
FIG. 4 is an elementary electric diagram of a second embodiment of the device, according to the invention.

An automatic increase in the load current, the load being in fact the patient's face skin located between the active electrode 9 and the passive electrode 10, in the course of dental electroanalgesia procedure, makes it possible to maintain efficient electrostimulation of the reflexogenic zone of the auricular concha in response to increased threshold value of pain appreciation. However, an increase in the mean value of electrostimulation current might inflict painful sensations upon the reflexogenic zone of the patient's concha or its "breakdown" and insufficiently opiate-mediated analgesic effect on the patient's organism. An automatic adjustment of the mean value of electric pulses in the course of dental electroanalgesia is carried out by the electric pulse repetition frequency regulator 34 (FIG. 3).

The electric pulse repetition frequency regulator 34 is controlled by the temperature sensor 11. As soon as the temperature of the patient's face skin rises at the place of application of the temperature sensor 11 its resistance value drops, the transistor 35 (FIG. 4) of the regulator 34 is disabled and its internal resistance increases, which in turn reduces the repetition frequency of electric pulses due to a higher resistance of the discharge circuit in the capacitor 16 of the generator 1.

The diodes 38, 39 perform electric isolation of the output of the temperature sensor 11 and the electric pulse duration regulator 12 from the electric pulse repetition frequency regulator 34.

The value of the electric pulse repetition frequency is substantially in linear relationship (with some approximation) to the patient's face skin. Thus, simultaneous increase in the duration of electric stimuli (pulses) and reduction or the electric pulse repetition frequency make it possible to maintain a stable mean value of electric stimuli applied, which in turn enables one to attain higher opiate-mediated analgesic effect on the patient's organism.

The proposed device have been trialled in therapeutic and orthopedic dentistry clinics. Application of the device makes it possible to carry out painless preparation of hard dental tissues in 98 percent of cases in operative treatment of caries and in 95 percent of cases in teeth preparation for fixed partial dentures.

Given below is an example of practical application of the device for dental electroanalgesia, according to the invention.

Patient's diagnosis is one of the defects of the maxillary teeth of the third class after Kennedy. Teeth preparation for artificial crowns is indicated.

The active electrode is smeared with an electrode paste and placed in the area of the reflexogenic zone of the auricular concha, that is, in the middle of the auricular lobule under the tragus and is fixed in position by a holder. The passive electrode is placed on the mucosa of the vestibular surface of the alveolar process of the upper jaw in the area of the projection of the root apices of the teeth being prepared.

The temperature sensor is placed on the patient's face skin at the place of the projection of the right infraorbital foramen and is secured in position with a piece of plaster. Next the device is turned in and an electric pulse repetition frequency of 15 Hz is adjusted by means of the frequency setter 2, and an electric pulse amplitude of 1.0 mA is set by the regulator 7 against the patient's subjective sensation of intense vibration in the area of the reflexogenic zone. For the following 15 minutes the skin temperature in the area of the right infraorbital foramen rises from 33.5° to 37.0° C. In the course of the dental electroanalgesia procedure the electric pulse repetition frequency reduces to 2 Hz, whereas the duration of electric pulses increases from 101 μs to 400 μs. The mean value of electric pulse amplitude remains nearly stable, ranging within 1.7 to 6.6 mA. Electrostimulation was continued throughout the whole period of teeth preparation. In the course of the teeth preparation there is noticed stable indices of peripheral hemodynamics; no painful sensations are felt by the patient.

Clinical application of the device makes it possible to cut down the treatment costs per patient 2.5 to 3.0 times and to increase the scope of stomatological service 15 to 16 times. Use of the device enables one to prognosticate the clinical effect of electrosimulation analgesia, to increase the adequacy of anesthesiologic stimulation 3 or 4 times, to enhance electroanalgesia efficacy and to reduce by 20 to 40 percent the time within which an analgesic effect is attained.

What is claimed is:

1. A device for dental electroanalgesia, comprising:
   at least two electrodes; a first electrode placed on a corresponding reflexogenic zone of the auricular concha; a second electrode placed on the mucosa of the alveolar process of one of the jaws within the area of the projection of the root apices of the patient's teeth being prepared;
   a low-frequency electric pulse generator having a first adjustment input and an output;
   an electric pulse repetition frequency setter having an output connected to the first adjustment input of said low-frequency electric pulse generator;
   an electric pulse front discriminator having an input and an output and connected with its input to the output of said low-frequency electric pulse generator;
   an electric pulse shaper having a first input, a second input, and an output and connected with its first input to the output of said electric pulse front discriminator;
   a current amplifier having an input and an output and connected with its input to the output of said electric pulse shaper;
   a transformer having an input and an output and connected with its input to the output of said current amplifier;
   an electric pulse amplitude regulator having an input and an output and connected with its input to the output of said transformer, while its output is electrically connected to said electrodes;
   a temperature sensor having an output and placed on the patient's face skin in the area of segmental innervation of the patient's dental tissue being prepared;
   an electric pulse duration regulator having an input and an output and connected with its input to the output of said temperature sensor and with its output to a second input of said electric pulse shaper.

2. The device of claim 1 wherein
   said low-frequency electric pulse generator having a second adjustment input; said device further comprising,
   an electric pulse repetition frequency regulator having an input connected to the output of said temperature sensor and an output connected to a second adjustment input of said low-frequency electric pulse generator.

* * * * *